United States Patent [19]

Simpson

[11] Patent Number: 5,039,004

[45] Date of Patent: Aug. 13, 1991

[54] MEDICAL APPLIANCE DISPOSAL CONTAINER

[75] Inventor: James L. Simpson, Indialantic, Fla.

[73] Assignee: Hemox Corporation, Indialantic, Fla.

[21] Appl. No.: 449,678

[22] Filed: Dec. 12, 1989

Related U.S. Application Data

[63] Continuation-in-part of Ser. No. 300,946, Jan. 24, 1989, Pat. No. 4,927,076.

[51] Int. Cl.$^5$ ............................................. B65D 5/06
[52] U.S. Cl. ................................... 229/132; 206/366; 206/571; 220/908; 229/907
[58] Field of Search ............... 206/366, 370, 571, 806, 206/621.5, 621.6, 621.7, 631.2; 220/908; 229/132, 134, 135, 907

[56] References Cited

U.S. PATENT DOCUMENTS

| | | | |
|---|---|---|---|
| 1,708,700 | 4/1929 | Maier | 229/135 |
| 2,291,753 | 8/1942 | Patten | 229/907 |
| 2,353,762 | 7/1944 | Robinson et al. | 229/3.1 |
| 2,549,048 | 4/1951 | Bergstein | 229/131 |
| 2,751,136 | 6/1956 | Moore | 229/132 |
| 3,089,633 | 5/1963 | Renshaw | 229/907 |
| 3,096,921 | 7/1963 | Graybill | 206/621.7 |
| 3,137,432 | 6/1964 | Rein et al. | 229/3.5 R |
| 3,294,618 | 12/1966 | Busche et al. | 229/3.1 |
| 3,355,085 | 11/1967 | Lindstrom | 229/3.1 |
| 3,770,185 | 11/1973 | Reeves | 206/621.7 |
| 3,958,056 | 5/1976 | Brugh, Jr. et al. | 229/3.1 |
| 4,121,755 | 10/1978 | Meseke et al. | 206/366 |
| 4,315,592 | 2/1982 | Smith | 206/366 |
| 4,452,358 | 6/1984 | Simpson | 206/366 |
| 4,534,489 | 8/1985 | Bartlett | 206/366 |
| 4,583,679 | 4/1986 | Johnson | 229/3.1 |
| 4,674,676 | 6/1987 | Sandel et al. | 206/366 |
| 4,702,385 | 10/1987 | Shillington et al. | 220/908 |
| 4,779,736 | 10/1988 | Geasland | 206/806 |
| 4,863,052 | 9/1989 | Lambert | 220/908 |
| 4,927,076 | 5/1990 | Simpson | 220/908 |

Primary Examiner—Gary E. Elkins
Attorney, Agent, or Firm—Evenson, Wands, Edwards, Lenahan & McKeown

[57] ABSTRACT

A discarded medical material container comprises a body of sheet material having laminated layers of compact fibrous material and material that is effectively impervious to the passage of fluid. The sheet material is formed into foldable panels that are joined together to define a bottom, sidewalls and a top of the body. The top has a closeable opening for the insertion of discarded material into the container and a closure tab. The top is formed of a first, interior panel of the sheet material having a region that is sectioned to define a plurality of flaps extending inwardly from the contour of the region, so as to define an opening in the first panel of sheet material, and a second, outer panel of sheet material, disposed atop the first panel. The second panel has a cut to define an aperture in the shape of a generally flexible tab overlying the region in the first panel and sized to close the aperture. A slit-score causes each flap to assume a generally downwardly bent condition. The slit-score is adjacent to and set back beneath an edge of the cut through the second panel, so that a portion of the second panel extends over the slit-score, thereby effectively preventing each flap from being bent outwardly through the aperture in the second panel.

20 Claims, 2 Drawing Sheets

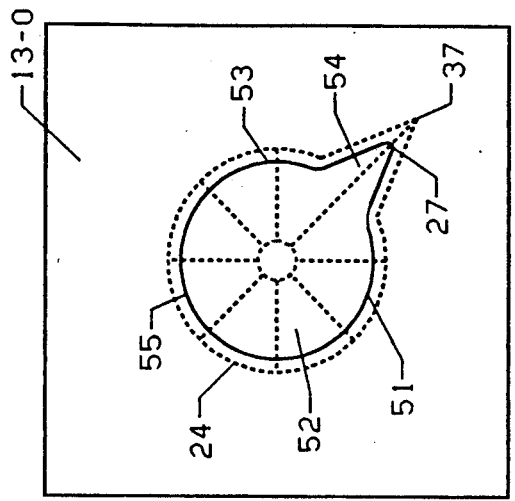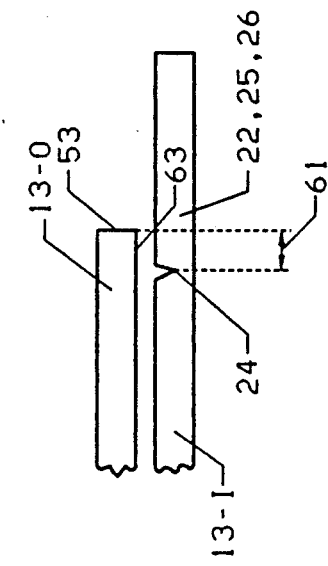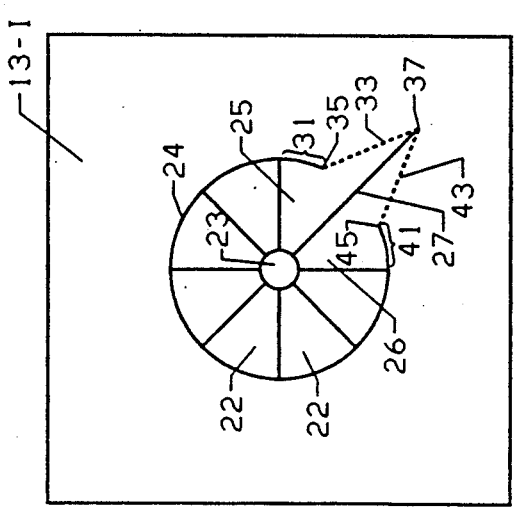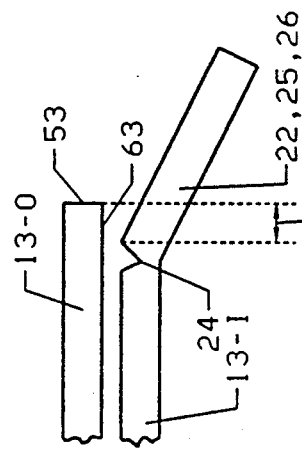

MEDICAL APPLIANCE DISPOSAL CONTAINER

CROSS REFERENCE TO RELATED APPLICATION

The present application is a continuation-in-part of copending application Ser. No. 300,946, filed Jan. 24, 1989, entitled Medical Appliance Disposal Container, and assigned to the assignee of the present application, now U.S. Pat. No. 4,927,076 issued May 22, 1990.

FIELD OF THE INVENTION

The present invention relates in general to the disposal of hazardous and potentially hazardous materials and is particularly directed to a new and improved container for the safe disposal of medical appliances such as syringes, scalpel blades, laboratory culture slides, blood tubing, toxic waste vessels, etc.

BACKGROUND OF THE INVENTION

In my above-referenced copending patent application, the disclosure of which is incorporated herein, there is described a new and improved medical appliance disposal container which is designed to meet or exceed requirements set forth in advisories issued by public health service organizations, such as the Center for Disease Control in Atlanta, Ga., governing the disposal of medical waste (including sharp instruments, such as scalpels and syringes). These advisories state that such containers must be rigid, leakproof and puncture resistant.

As pointed out in that application, many of the medical waste material containers that are currently employed by the medical community are typically multi-piece plastic structures, usually of 'snap together' construction, which not only are susceptible to leaks at their joints, but often readily come apart, spilling their contents, when subjected to 'trash removal' type of handling by hospital custodial personnel. Moreover, because hospital regulations often require destruction by incineration, burning containers made substantially entirely of plastic can cause the emission of considerable quantities of toxic pollutants, such as HCl and dioxins.

To successfully solve these problems the medical appliance disposal container described in my above-referenced application has a unitary body structure formed of a substantially flat sheet of laminated layers of compact, non-toxic, fibrous material, such as high bond strength (on the order of 500 Mullen) fiberboard, which is effectively impermeable to needle punctures. This laminated sheet structure is also provided, preferably at least within its interior, with one or more thin (on the order of one to several mils) pliable layers of an absorption resistant material, such as polyethylene, that forms a liquid barrier and thereby prevents the passage of fluid through the entirety of the fibrous material and thus serves to maintain the integrity and strength of the wall structure of the container.

In the course of manufacture of the container, the sheet material is divided into a plurality of foldable panels that are scored, wrapped at corners and adhesively joined together to define a bottom, sidewalls and a top of the body structure. The panels are scored along lines spaced apart from folded edges, so as to form beads in the sheet material that are separated from the corners of folds, whereby edges of the panels abut against corners of the folds and ensure a snug, leakproof fit of the panels.

In accordance with one of the embodiments of the container (which may be substantially cube or square-shaped), an outer top panel of the container is provided with a generally circular aperture, from which a narrow, generally triangular or 'V'-shaped cut-out region extends. An interior top panel, directly beneath the outer top panel, has a region that is sectioned into wedge-shaped flaps, that are bent downwardly into the container. A smaller, central circular aperture in the interior to panel beneath the outer top panel defines the interior edge of the wedge-shaped flaps. The wedge-shaped flaps are bent inwardly from a slit score line, which follows the generally circular shape of the aperture in the outer top panel of the container. The slit score line is slightly behind the lip of the outer top panel and causes the wedge shape tabs to remain in their generally downwardly bent condition and a pair of adjacent, downwardly bent flaps beneath the 'V'-shaped cut-out region form a narrow slot which extends from the central aperture to the vertex of the 'V'-shaped region to provide a converging 'crimping' region whereat needles may be bent when discarding a syringe.

The outer top panel also has a closure tab the perimeter of which is coincident with the circular/'V'-shaped opening in the outer top panel and extends from a slit score along a line at a fold location of the closure tab. The slit score causes the closure tab to be retained in a generally upwardly or outwardly extending condition. The score line in the outer top panel is relatively short, so that the closure tab, when urged down into its original position, will not tend to resist remaining in the horizontal position and can be readily sealed by an overlying plastic label.

SUMMARY OF THE INVENTION

Now, although the central aperture and wedge-shaped flaps in the interior top panel facilitate ease of entry of discarded medical devices (e.g. syringes) and, at the same time, prevent their removal, it has been found that the functionality of the wedge-shaped flaps can be improved by changing the location of the slit score line that follows the perimeter of the aperture in the top outer panel, so as to effectively prevent the flaps in the interior top panel from having any tendency to be bent upwardly away from the container opening.

More particularly, in the (cube shaped) container described in the above-referenced application, the slit score line, from which the wedge-shaped flaps in the interior panel are bent downwardly into the container, is slightly separated toward the central small aperture at the ends of the wedge-shaped flaps, adjacent to the edge or lip of the aperture in the outer top panel. This separation or interior displacement of the slit score means that the entirety of each of the tabs, except those beneath the 'V'-shaped opening, including the slit score, is exposed. As a consequence if a discarded device should become lodged or partially inserted into the container, inadvertent pulling on the device may apply an outwardly directed force against an end edge of a flap, making it tend to bend outwardly and enlarge the opening in the container.

In accordance with the present invention, this possibility is effectively eliminated by locating the slit score in the interior outer panel, from which the flaps are bent downwardly into the container, along a line that is set back beneath the outer top panel, apart from the edge of the aperture that is closed by the closure tab. By setting the slit score line back underneath the outer top panel, the slit score and a top end portion of each wedge-shaped flap is covered by an overhang that provides an effective barrier against the outward bending of the flap, away from its normally downwardly urged condition.

BRIEF DESCRIPTION OF THE DRAWINGS

FIGS. 2 and 3 show a top view of the interior and outer top panels of the medical appliance disposal container in FIG. 1; and FIGS. 4 and 5 are diagrammatic cross-sectional illustrations of a portion of the interior and outer top panels of FIGS. 2 and 3, respectively.

DETAILED DESCRIPTION

Figure 1:
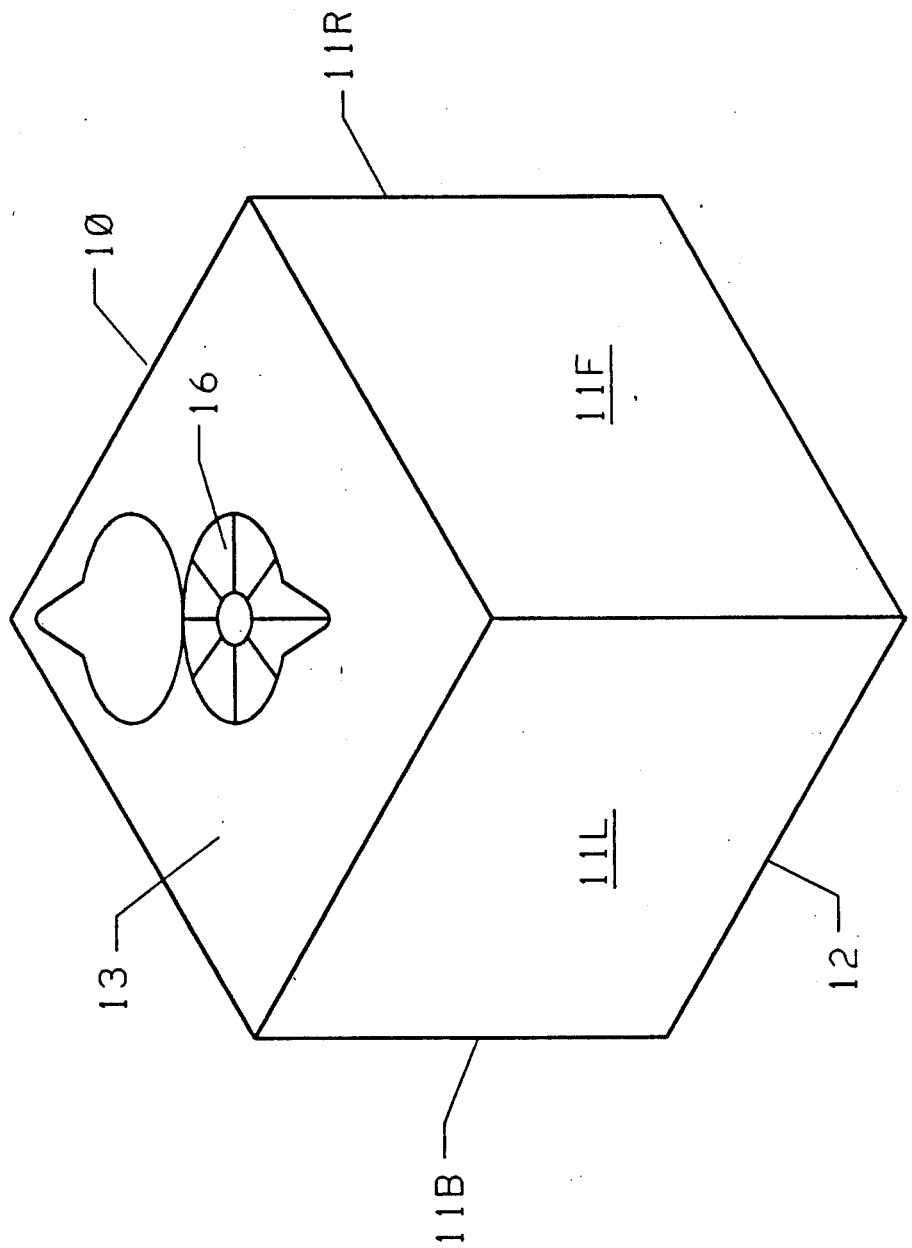
FIG. 1 is a pictorial illustration of an embodiment of a medical appliance disposal container which is provided with a generally circular aperture in its top.

As described above, the present invention is directed to an improvement in an embodiment of a medical appliance disposal container detailed in my above-referenced copending application, in which an outer top panel of the container is provided with a generally circular aperture, from which a narrow, generally triangular or 'V'-shaped cut-out region extends. The overall configuration of such a container is shown in perspective in FIG. 1 as comprising a generally square, or cube-shaped, body 10 having a plurality of (four) sides 11, a bottom 12 and a top 13. In the generally cube-shaped configuration shown in FIG. 1, the body has a front 11F, a pair of parallel left and right sides 11L and 11R, respectively, and a back 11B parallel with front 11F. Each of bottom 12 and top 13 is contiguous with each of the sides 11. While bottom 12 has a continuous surface, top 13 has a generally circular aperture 16 of sufficient size for insertion of a medical appliance, such as a needle-syringe assembly or scalpel.

As described in my copending application, the material of which the container is made is preferably formed of laminate sheet material having plural layers of wood pulp fiber-based fiberboard, with an individual layer having a thickness on the order of 12-25 mils. Preferably, the fiberboard is extremely high strength material such as Kraft board supplied by Sunoco Fiber Drum, having a bond strength on the order of 450-550 Mullen (e.g. 500 Mullen). The fiberboard layers are adhesively laminated together using a conventional adhesive such as polyvinyl alcohol. Because of the high density, high Mullen bond strength of the fiberboard layers, the sheet material is extremely strong and is effectively needle-puncture proof. To provide a water seal barrier, one or more layers of fluid impervious material, such as a thin flexible plastic, is included as part of the laminate structure.

In one example of the construction of the fiberboard having two such layers, an inner flexible plastic layer is adhesively laminated (by way of polyvinyl alcohol adhesive) between two fiberboard layers, and an outer plastic layer is adhesively bonded by way of polyvinyl alcohol adhesive layer to an outer fiberboard layer. The fluid barrier-providing thin plastic layer may be formed of polyvinyl chloride or polyurethane, having a thickness on the order of 1 to several mils, so that it has elasticity. This flexible plastic material may be provided as a central or interior layer of the laminate structure, and/or as the outer surface. Also, the plastic material is preferably a high visibility material, to provide a hazardous waste warning to medical personnel, e.g. a bright red material, or a yellow orange to provide a clear contrast background for blood spatters. Manufacture of the laminate sheet material, per se, may be effected in a conventional manner, by feeding webs from respective rolls of fiberboard and plastic sheet stock through a rolling mill lamination station whereat an adhesive applicator and compression rolling mill secure the multiple layers together.

It should also be noted that while the laminate structure is preferably comprised of two pairs of fiberboard layers, the number employed is not limited. What is important, however, is that the structure be symmetric or "balanced". Namely, a single fiberboard layer having a layer of plastic on only one side thereof will tend to distort in one direction and not lay flat. Pairs of multiple fiberboard layers provide a balanced or symmetric arrangement of fiberboard layers about an intermediate thin plastic film layer, so that the sheet laminate will essentially lay flat. With an outer layer of plastic film, the overall thickness of the sheet laminate is typically on the order of 58-62 mils.

To provide further leakage protection an a coating of an absorption resistant material, such as polyvinyl alcohol, may be formed along the interior sidewalls and the interior bottom surface of the container. After the container has been assembled, this layer may be formed by pouring an absorption-resistant liquid, such as a commercially available non-toxic liquid glue, through the opening in the top of the container and allowing it to adhere to the sides and bottom so that it coats fold-/wrap lines. The interior surface of the sheet material may also include the above-mentioned plastic layer. Still, by providing this absorbent protection coating, the corners of the bottom and sides of the interior of the container are completely sealed after the liquid coating sets up and dries.

The structural configuration of the top 13 of the container is shown in greater detail in FIGS. 2 and 3 as having an interior top panel 13-I laminated with an outer top panel 13-O. As shown in FIG. 2, Interior top panel 13-I has a curvilinear or generally circular region 21 that is sectioned into a plurality of wedge-shaped flaps 22, that are slit-scored along a generally circular line 24 and bent downwardly into the container. A smaller, central circular aperture 23 is cut out in the center of panel 13-I and defines the interior edge 24 of each of flaps 22. It is to be noted that the generally circular slit score line 24 does not form a complete circle, but terminates partially across two of the flaps 25, 26, which are separated from each other by a deep cut line 27 that has a length greater than the approximate radius of the generally circular slit score line 24. As a consequence, the fold line from which flap 25 is bent downwardly into the container comprises a portion 31 of slit score 24 that terminates within flap 25 and a fold line 33 that extends from one end 35 of slit score 24 to a termination 37 of deep cut line 27. Similarly, the fold line from which flap 26 is bent downwardly into the container comprises a portion 41 of slit score 24 that terminates within flap 26 and a fold line 43 that extends from another end 45 of slit score 24 to the termination 37 of deep cut line 27. The termination 37 of deep cut line is such that fold lines 33 and 43 form a narrow triangular or 'V'-shaped fold line perimeter.

The slit score line 24 and 'V'-forming fold lines 33 and 43 from which flaps 22 are bent inwardly into the container follow the generally circular shape of an aperture 51 in outer top panel 13-O of the container, as shown in FIG. 3. Aperture 51, which has a shape substantially corresponding to the combination of the circular score line 24 and 'V'-forming fold line 33, 43 of interior panel 13-I, as shown by generally circular region 53 and 'V'-shaped region 54, is closable by a closure tab 53 from a score line 55 in the top surface of outer top panel 13-O. The diameter and shape of slit score line 24 interior top panel 13-I are slightly larger than those of aperture 53 in top outer panel 13-O such that, as shown in FIGS. 4 and 5, score line 24 (and also each of fold lines 33, 43) is set back from the edge of aperture 53, so that slit score line 24 is recessed underneath outer top panel 13-O. As a result, slit score 24 and a top end portion 61 of each wedge-shaped flap (22, 25, 26) is covered by an overhang region 63 of outer top panel 13-O, that provides an effective barrier against the outward bending of the flap, away from its normally downwardly urged condition.

The container is folded and assembled in the manner described in my copending application, whereby scoring of the sheet material of the respective panels is selectively located to enable the corners to be effectively wrapped in a very snug tight configuration, rather than folded, which might otherwise prevent a secure seal of the corners of the folds. In addition to scoring the wrapped edges of the sheet material at locations slightly displaced from the corners of the container, so as to cause the formation of the bead around the edge of a flap, the manufacturing process for producing the container preferably uses an energy source that causes a heating of the plastic material so that it becomes tacky and adhesive.

For this purpose a source of electromagnetic radiation, such as infrared light, may be employed. The energy source heats the plastic material to a tacky, adhesive state, so that the outer plastic layer, in effect, becomes the adhesive, thereby eliminating the need for a separate adhesive material to secure the panels of the container together. During manufacture, the respective panels and flaps of the container, which are to be joined together to form a structure such as that illustrated in FIG. 1, may be irradiated by electromagnetic radiation, such as that provided by an infrared lamp. The lamp irradiates the outer plastic layer for a period of time on the order of five to twenty seconds, which is sufficient to soften the outer plastic layer and render it tacky. The respective panels are then folded over and pressed against one another through a suitable folding medium, such as a Teflon or marble roller, which has no affinity for the plastic. Advantageously, the set-up time for such an irradiated plastic material is on the order of none to two seconds, so that the time required for the assembly of a container is reduced considerably in comparison with the case where a separate adhesive material is employed.

As will be appreciated from the foregoing description, the present invention improves the structural integrity of the flap-configured opening in the top panel of a medical waste disposal container described in the above-referenced copending application. As in the case of my earlier design, not only is the laminate structure effectively impermeable to punctures and leakproof, but, by setting back or recessing the slit score line for the insertion flaps in the top panel from the edge of the closure flap opening, the possibility of these flaps being bent outwardly is effectively eliminated, thereby increasing the security of the container.

While I have shown and described an embodiment in accordance with the present invention, it is to be understood that the same is not limited thereto but is susceptible to numerous changes and modifications as known to a person skilled in the art, and I therefore do not wish to be limited to the details shown and described herein but intend to cover all such changes and modifications as are obvious to one of ordinary skill in the art.

What is claimed is:

1. A discarded material container comprising a container body formed of substantially flat sheet material having a plurality of laminated layers of compact fibrous material and material that and is effectively impervious to the passage of fluid therethrough, said substantially flat sheet containing a plurality of foldable panels that are folded and joined together to define a bottom, sidewalls and a top of said body, said top having a closable opening therethrough for the insertion of discarded material into the container and a closure tab formed of and integrally foldable with respect to said sheet material, said closure tab being shaped and sized to close said closable opening when urged into said opening, and wherein said container top is formed of a first, interior panel of said sheet material having a region that is sectioned to define a plurality of flaps extending inwardly from the contour of said region, so as to define an opening in said first panel of sheet material, and a second, outer panel of said sheet material, disposed atop said first panel, said second panel having a cut therethrough to define an aperture in the shape of a generally flexible tab overlying said region in said first panel and being sized to effectively close said aperture when urged downwardly into said aperture, and wherein each of said plurality of flaps is formed of said first, interior panel of said sheet material and has a slit-score that causes each flap to assume a generally downwardly bent condition, said slit-score being adjacent to and set back beneath an edge of said cut through said second panel, so that a portion of said second panel extends over said slit-score, thereby effectively preventing each flap from being bent outwardly through the aperture in said second panel.

2. A discarded material container according to claim 1, wherein said region in said interior panel is a generally circular region sectioned to define a plurality of generally wedge-shaped tabs extending inwardly from the circular contour of said region, so as to define a generally circular opening in said first panel of sheet material, and wherein said second panel has a generally circular cut therethrough to define a generally circular aperture in the shape of said flexible tab overlying said generally circular region in said first panel and being sized to effectively close the generally circular opening in said first panel when urged downwardly into said aperture in said second panel.

3. A discarded material container according to claim 2, wherein said generally circular aperture further includes a tapered aperture portion extending from a generally circular aperture portion, and wherein two adjacent ones of said flaps are separated from one another by a slit that lies within the confines of said tapered aperture portion.

4. A discarded material container according to claim 3, wherein opposite ends of said slit score terminate within said adjacent ones of said flaps, so that a fold line, recessed beneath an edge of said cut, extends from said opposite ends of said slit score to the termination of slit.

5. A discarded material container according claim 1, wherein said laminate structure is comprised of plural layers of said compact fibrous material and plural layers of material that is effectively impervious to the passage of fluid therethrough.

6. A discarded material container according claim 5, wherein said laminate structure is configured such that one layer of said plural layers of material that is effectively impervious to the passage of fluid therethrough forms an external surface of said body.

7. A discarded material container according claim 6, wherein an external outer surface of said body has a high visibility color.

8. A discarded material container according claim 7, wherein another of said layers of material that is effectively impervious to the passage of fluid therethrough is separated from said one layer by a layer of compact fibrous material therebetween.

9. A discarded material container according claim 1, wherein intersections of interior surfaces of said bottom and sidewalls of said body are coated with a material that is effectively impervious to the passage of fluid therethrough.

10. A discarded material container according claim 1, wherein said body is comprised of a folded unitary laminate structure.

11. A discarded material container according claim 10, wherein said folded unitary laminate structure is configured such that a layer of pliable plastic forms one surface of said sheet, and wherein folded contiguous panels are adhesively joined together by said layer of pliable plastic.

12. A discarded material container according claim 1, wherein the top, sidewalls and bottom of said container body are formed of a substantially flat sheet of said laminate structure having a plurality of foldable panels that are scored, folded and joined together such that, at the location of a fold in said substantially flat sheet of said laminate structure to form a corner of said container body, a sheet panel is scored on one side thereof at a region adjacent to the location of the fold, so as to cause the protrusion of a bead on an opposite, interior side of said sheet panel, whereby a side edge of a foldable sheet panel abuts against an interior fold corner of another sheet panel that has been folded to be contiguous therewith and is captured between said bead and said interior fold corner of said another sheet panel, thereby effectively providing a sealed joint thereat and preventing the formation of a leakage space between the interior of said container and the exterior thereof.

13. A discarded material container comprising a container body formed of substantially flat sheet material having a plurality of laminated layers of compact fibrous material and material that is effectively impervious to the passage of fluid therethrough, said substantially flat sheet containing a plurality of foldable panels that are folded and joined together to define a bottom, sidewalls and a top of said body, said top having a closable opening therethrough for the insertion of discarded material into the container and a closure tab formed of and integrally foldable with respect to said sheet material, said closure tab being shaped and sized to close said closable opening when urged into said opening, and wherein said container top is formed of a first, interior panel of said sheet material having a generally curvilinear region and a generally tapered portion extending therefrom that is sectioned to define a plurality of flaps extending inwardly from the contour of said region, so as to define an opening in said first panel of sheet material, and a second, outer panel of said sheet material, disposed atop said first panel, said second panel having a cut therethrough to define an aperture, closable by a corresponding generally flexible tab, overlying and in the shape of the generally curvilinear region and generally tapered portion of said first, interior panel, when said is urged downwardly into said aperture, and wherein each of said plurality of flaps is formed of said first, interior panel of said sheet material and has a slit-score that causes each flap to assume a generally downwardly bent condition, said slit-score being adjacent to and set back beneath an edge of said cut through said second panel, so that an overhang portion of said second panel extends over said slit-score, thereby effectively preventing each flap from being bent outwardly through the aperture in said second panel.

14. A discarded material container according to claim 13, wherein said curvilinear region in said interior panel is a generally circular region sectioned to define a plurality of generally wedge-shaped tabs extending inwardly from the circular contour of said region, so as to define a generally circular opening in said first panel of sheet material, and wherein said second panel has a generally circular cut therethrough to define a generally circular aperture in the shape of said flexible tab overlying said generally circular region of said first panel and being sized to effectively close the generally circular region of said first panel when urged downwardly into said aperture in said second panel.

15. A discarded material container according to claim 14, wherein two adjacent ones of said flaps are separated from one another by a slit that lies within the confines of said tapered portion.

16. A discarded material container according to claim 15, wherein opposite ends of said slit score terminate within said adjacent ones of said flaps, so that a fold line, recessed beneath an edge of said cut, extends from said opposite ends of said slit score to the termination of slit.

17. A discarded material container according claim 13, wherein said laminate structure is comprised of plural layers of said compact fibrous material and plural layers of material that is effectively impervious to the passage of fluid therethrough.

18. A discarded material container according claim 17, wherein said laminate structure is configured such that one layer of said plural layers of material that is effectively impervious to the passage of fluid therethrough forms an external surface of said body.

19. A discarded material container according claim 13, wherein intersections of interior surfaces of said bottom and sidewalls of said body are coated with a material that is effectively impervious to the passage of fluid therethrough.

20. A discarded material container according claim 13, wherein the top, sidewalls and bottom of said container body are formed of a substantially flat sheet of said laminate structure having a plurality of foldable panels that are scored, folded and joined together such that, at the location of a fold in said substantially flat sheet of said laminate structure to form a corner of said container body, a sheet panel is scored on one side thereof at a region adjacent to the location of the fold, so as to cause the protrusion of a bead on an opposite, interior side of said sheet panel, whereby a side edge of a foldable sheet panel abuts against an interior fold corner of another sheet panel that has been folded to be contiguous therewith and is captured between said bead and said interior fold corner of said another sheet panel, thereby effectively providing a sealed joint thereat and preventing the formation of a leakage space between the interior of said container and the exterior thereof.

* * * * *